(12) United States Patent
Parvulescu et al.

(10) Patent No.: US 9,540,305 B2
(45) Date of Patent: Jan. 10, 2017

(54) PROCESS FOR PREPARING ACRYLIC ACID USING AN ALKALI METAL-FREE AND ALKALINE EARTH METAL-FREE ZEOLITIC MATERIAL

(71) Applicant: BASF SE, Ludwigshafen (DE)

(72) Inventors: Andrei-Nicolae Parvulescu, Ruppertsberg (DE); Armin Lange De Oliveira, Heidelberg (DE); Stephan A. Schunk, Heidelberg-Rohrbach (DE); Nicolai Tonio Woerz, Darmstadt (DE); Marco Hartmann, Woerth (DE); Kazuhiko Amakawa, Mannheim (DE); Michael Goebel, Mannheim (DE); Yong Liu, Limburgerhof (DE); Michael Lejkowski, Neckargemuend (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/724,244

(22) Filed: May 28, 2015

(65) Prior Publication Data

US 2015/0344394 A1    Dec. 3, 2015

Related U.S. Application Data

(60) Provisional application No. 62/005,011, filed on May 30, 2014.

(30) Foreign Application Priority Data

May 30, 2014    (DE) .................... 10 2014 008 081

(51) Int. Cl.
*C07C 51/347*    (2006.01)
*C07C 51/353*    (2006.01)
(Continued)

(52) U.S. Cl.
CPC .......... *C07C 51/347* (2013.01); *C07C 51/353* (2013.01); *B01J 29/82* (2013.01); *B01J 29/83* (2013.01);
(Continued)

(58) Field of Classification Search
CPC ...... C07C 51/353; C07C 57/04; C07C 51/347; C07C 2529/04; C07C 2529/064; C07C 2529/076; C07C 2529/80; C07C 2529/82; C07C 2529/83; C07C 2529/84; C07C 2529/85; B01J 29/06; B01J 29/061; B01J 2029/062; B01J 29/076; B01J 29/80; B01J 29/82; B01J 29/83; B01J 29/84; B01J 29/85
(Continued)

(56) References Cited

U.S. PATENT DOCUMENTS 3,720,756 A * 3/1973 Schwochow ....... C01B 33/2846
423/710
4,118,588 A * 10/1978 Fouquet ................ C07C 51/353
502/208
(Continued)

FOREIGN PATENT DOCUMENTS

| DE | 10 2010 040 921 A1 | 3/2012 |
| DE | 10 2010 040 923 A1 | 3/2012 |
| WO | WO 2013/117537 A1 | 8/2013 |

OTHER PUBLICATIONS

Piotr T. Wierzchowski, et al., "Aldol Condensation in Gaseous Phase by Zeolite Catalysts" Catalysis Letters, vol. 9, 1991, pp. 411-414.
(Continued)

*Primary Examiner* — Jafar Parsa
*Assistant Examiner* — Amy C Bonaparte
(74) *Attorney, Agent, or Firm* — Oblon, McClelland, Maier & Neustadt, L.L.P.

(57) ABSTRACT

A process for preparing acrylic acid, comprising (i) providing a stream S4 comprising a formaldehyde source and acetic acid; (ii) contacting stream S4 with an aldol condensation catalyst comprising a zeolitic material comprising aluminum in the framework structure to obtain a stream S6 comprising acrylic acid, the framework structure of the zeolitic material in (ii) comprising $YO_2$ and $Al_2O_3$, and Y being a tetravalent element; where the total content of alkali metal and alkaline earth metal in the zeolitic material in (ii), calculated as alkali metal oxide and alkaline earth metal oxide, is from 0% to 0.1% by weight, based in each case on the total weight of the zeolitic material, and where the aldol condensation catalyst in (ii) comprises, outside the framework structure of the zeolitic material present therein, from 0% to 1% by weight of vanadium, based on vanadium as vanadium(V) oxide.

15 Claims, 1 Drawing Sheet

(51) Int. Cl.
  *B01J 29/82* (2006.01)
  *B01J 29/84* (2006.01)
  *B01J 29/83* (2006.01)
  *B01J 29/85* (2006.01)

(52) U.S. Cl.
  CPC .............. *B01J 29/84* (2013.01); *B01J 29/85* (2013.01); *C07C 2529/82* (2013.01); *C07C 2529/83* (2013.01); *C07C 2529/84* (2013.01); *C07C 2529/85* (2013.01)

(58) Field of Classification Search
  USPC ........................................................ 562/599
  See application file for complete search history.

(56) References Cited

U.S. PATENT DOCUMENTS

| | | | |
|---|---|---|---|
| 4,677,225 A * | 6/1987 | Niizuma | B01J 27/18 560/214 |
| 2004/0076554 A1 * | 4/2004 | Kuechler | B01J 8/0055 422/139 |
| 2012/0071687 A1 | 3/2012 | Herzog et al. | |
| 2012/0071688 A1 | 3/2012 | Herzog et al. | |
| 2013/0085294 A1 | 4/2013 | Peterson et al. | |
| 2013/0267737 A1 * | 10/2013 | Mueller | C07C 51/353 562/599 |

OTHER PUBLICATIONS

James F. Vitcha, et al., "Vapor Phase Aldol Reaction: Acrylic Acid by the Reaction of Acetic Acid and Formaldehyde" I & EC Product Research and Development, vol. 5, No. 1, Mar. 1966, pp. 50-53.

* cited by examiner

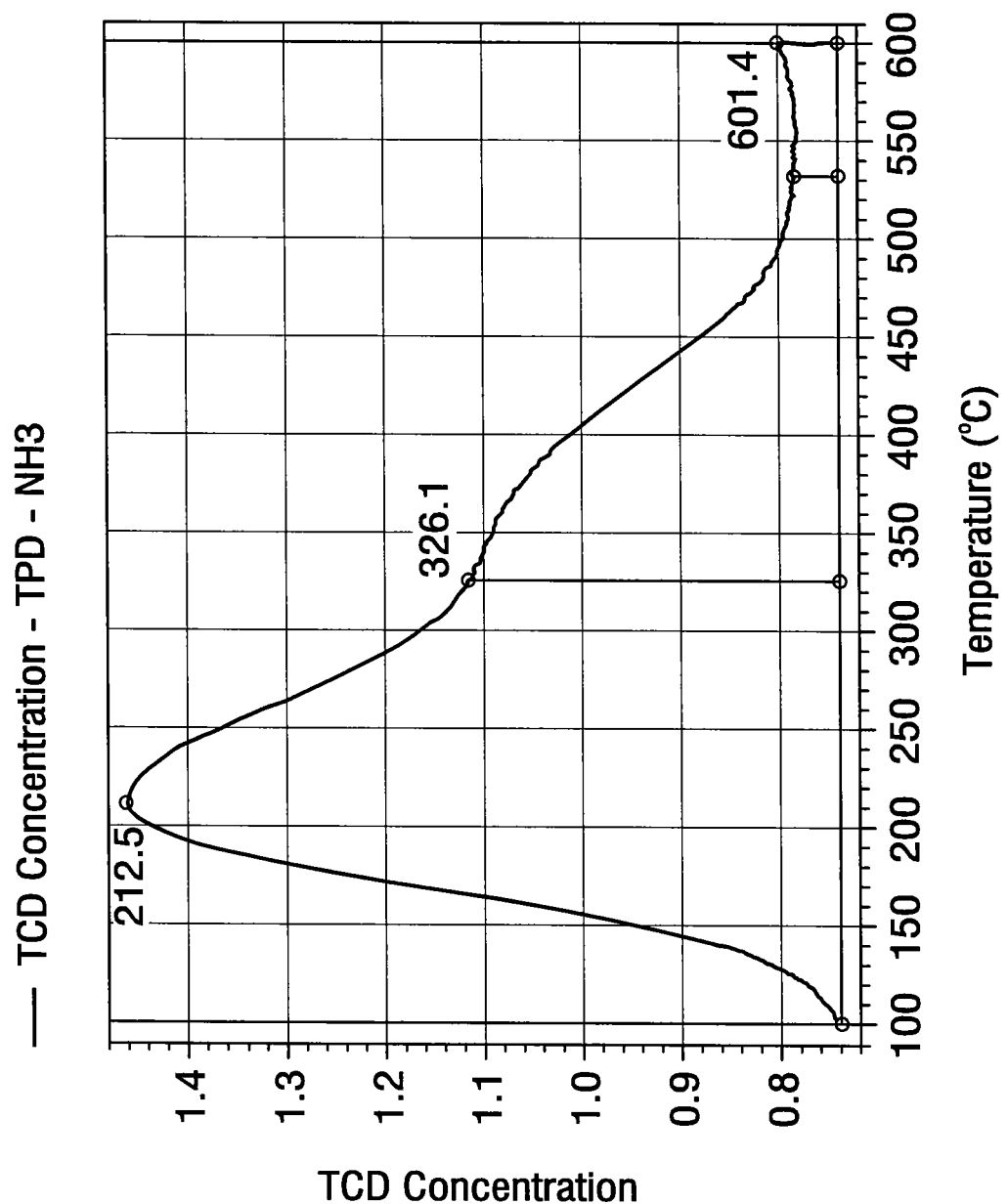

PROCESS FOR PREPARING ACRYLIC ACID USING AN ALKALI METAL-FREE AND ALKALINE EARTH METAL-FREE ZEOLITIC MATERIAL

The present invention relates to a process for preparing acrylic acid by contacting a stream comprising a formaldehyde source and acetic acid with an aldol condensation catalyst comprising an alkali metal-free and alkaline earth metal-free zeolitic material.

Acrylic acid, an important monomer for production of homo- and copolymers, is typically obtained by a heterogeneously catalyzed two-stage partial oxidation proceeding from propene, with acrolein as intermediate.

Vitcha and Sims, I & EC Product Research and Development, Vol. 5, No. 1, March 1966, pages 50 to 53, describe the synthesis of acrylic acid in a gas phase reaction proceeding from acetic acid and formaldehyde. Catalysts described are firstly aluminosilicates wherein the negative framework charges are preferably compensated for by alkali metal and alkaline earth metal ions. A second type of catalyst described is hydroxide from the group consisting of alkali metal hydroxides, alkaline earth metal hydroxides and aluminum hydroxide (preferably KOH, NaOH, $Ca(OH)_2$ and $Mg(OH)_2$), applied to the inert supports (e.g. amorphous silicon dioxide).

Wierzchowsky and Zatorski, Catalysis Letters 9 (1991), pages 411 to 414, describe the aldol condensation of formaldehyde prepared in situ with methyl propionate in the gas phase over various zeolitic catalysts.

DE 2010 040 921 A1 discloses a process for preparing acrylic acid from methanol and acetic acid, wherein methanol is first converted to formaldehyde and the latter is reacted with acetic acid to give acrylic acid. Preference is given to using catalysts wherein the active composition is a vanadium-phosphorus oxide and/or a vanadium-phosphorus oxide doped with elements other than vanadium and phosphorus.

DE 2010 040 923 A1 describes a process for preparing acrylic acid from ethanol and formaldehyde, wherein ethanol is first converted to acetic acid and the latter is reacted with formaldehyde to give acrylic acid. Here, preference is likewise given to using catalysts wherein the active composition is a vanadium-phosphorus oxide and/or a vanadium-phosphorus oxide doped with elements other than vanadium and phosphorus.

US 2013/0085294 A1 discloses a process for preparing acrylic acid from acetic acid and an alkylating agent such as formaldehyde. The catalysts used comprise titanium and vanadium, and optionally oxidic additives such as $SiO_2$, $Al_2O_3$ and $ZrO_2$. For the merely optional supporting of the catalytically active component, zeolitic materials are among those mentioned as supports.

In spite of the numerous processes developed for preparation of acrylic acid, there was still a need to develop an improved process for preparing acrylic acid proceeding from a formaldehyde source and acetic acid. One of the problems addressed by the present invention was therefore that of providing an improved process for preparing acrylic acid proceeding from a formaldehyde source and acetic acid.

It has been found that, surprisingly, such an improved process for preparation can be provided when an aldol condensation catalyst comprising a specific zeolitic material as catalytically active component is used. More particularly, it has been found that the improved process stands out in a positive way from the known processes in terms of at least one of the parameters of carbon conversion, yield of acrylic acid, selectivity of acrylic acid formation and space-time yield, and the process improved in accordance with the invention especially also stands out in a positive way from the known processes in terms of all these parameters.

The present invention therefore relates to a process for preparing acrylic acid, comprising
(i) providing a stream S4 comprising a formaldehyde source and acetic acid;
(ii) contacting stream S4 with an aldol condensation catalyst comprising a zeolitic material comprising aluminum in the framework structure to obtain a stream S6 comprising acrylic acid, the framework structure of the zeolitic material in (ii) comprising $YO_2$ and $Al_2O_3$, and Y being a tetravalent element;
where the total content of alkali metal and alkaline earth metal in the zeolitic material in (ii), calculated as alkali metal oxide ($M_2O$) and alkaline earth metal oxide (MO), is from 0% to 0.1% by weight, based in each case on the total weight of the zeolitic material, and
where the aldol condensation catalyst in (ii), outside the framework structure of the zeolitic material present in the aldol condensation catalyst, comprises from 0% to 1% by weight of vanadium, calculated as vanadium(V) oxide and based on the total weight of the aldol condensation catalyst.

The term "aldol condensation" as used in the context of the present invention is understood to mean a condensation reaction in which an alpha,beta-unsaturated carbonyl compound, acrylic acid in the present case, is formed from two suitable carbonyl compounds, acetic acid and formaldehyde in the present case, with elimination of water.

Step (i)

In step (i) of the process according to the invention, a stream S4 comprising a formaldehyde source and acetic acid is provided.

A useful formaldehyde source for the process according to the invention is in principle any suitable formaldehyde source which affords formaldehyde under the conditions of the contacting in (ii) or in the provision in (i). The formaldehyde source is preferably anhydrous. According to the present invention, the formaldehyde source is preferably selected from the group consisting of formaldehyde, trioxane, paraformaldehyde and a mixture of two or more thereof. In a particularly preferred embodiment of the present invention, trioxane is used as formaldehyde source, and trioxane is further preferably used as the sole formaldehyde source in the process. Trioxane is a heterocyclic compound from the group of the acetals, which forms through trimerization of formaldehyde and depolymerizes again on heating to 150 to 200° C. to give monomeric formaldehyde. Paraformaldehyde is the short-chain polymer of formaldehyde, typically having a degree of polymerization of 8 to 100.

A useful source for the acetic acid is in principle any suitable source comprising at least a proportion of acetic acid, preference being given to preferably acetic acid having a purity of 95 to 100% by weight, further preferably 96 to 100% by weight, further preferably 97 to 100% by weight, further preferably 98 to 100% by weight, further preferably 99 to 100% by weight. Particular preference is given to the acetic acid in pure form as glacial acetic acid.

Stream S4 may in principle have any molar ratio of acetic acid to formaldehyde suitable for obtaining acrylic acid in the process according to the invention, formaldehyde being obtained and/or obtainable from the formaldehyde source. Preferably, the molar ratio of acetic acid to formaldehyde, obtained and/or obtainable from the formaldehyde source, in stream S4 is in the range from 0.01:1 to 10:1. Further preferably, the molar ratio of acetic acid to formaldehyde, obtained and/or obtainable from the formaldehyde source, in stream S4 is in the range from 0.1:1 to 9:1, further preferably from 0.5:1 to 8.5:1. Further preferably, the molar ratio of acetic acid to formaldehyde, obtained and/or obtainable from the formaldehyde source, in stream S4 is in the range from 1:1 to 8:1, further preferably from 1.5:1 to 5:1, further preferably from 1.7:1 to 4.7:1, further preferably from 2:1 to 4.4:1, further preferably from 2.5:1 to 4.1:1.

In principle, stream S4 can be provided at any temperature suitable for the process according to the invention. Stream S4 can therefore be provided, for example, at a temperature corresponding to room temperature, or else be heated prior to contacting with an aldol condensation catalyst comprising a zeolitic material to obtain a stream S6 comprising acrylic acid. If stream S4 is heated, the heat sources in the context of the process according to the invention are unrestricted, and so any heat source is useful in principle. Thus, it is also possible that stream S4 is heated with the aid of a product stream of the present process. For example, stream S4 can be heated to a temperature of 190° C. or 200° C. It is equally conceivable that stream S4 is cooled to a temperature suitable for the process according to the invention, if individual components or else all the components of stream S4 would otherwise have an undesirably high temperature for the process according to the invention. For the process according to the invention, it is preferable that stream S4 is brought to a temperature of 150 to 250° C. before being contacted with an aldol condensation catalyst comprising a zeolitic material to obtain a stream S6 comprising acrylic acid. It is further preferable that stream S4 is brought to a temperature of 180 to 220° C. before being contacted with an aldol condensation catalyst comprising a zeolitic material to obtain a stream S6 comprising acrylic acid.

As well as acetic acid and a formaldehyde source, the stream S4 provided in (i) may comprise further components. For example, diluents are an option here. It is possible here to use all suitable diluents which are known to those skilled in the art and allow performance of the process according to the invention to obtain acrylic acid. The diluents are preferably selected from the group consisting of nitrogen, carbon monoxide, carbon dioxide, ethene, acetone, water and a combination of two or more thereof. Further preferably, the diluent comprises nitrogen. Consequently, the present invention also relates to a process wherein stream S4 further comprises one or more diluents, preferably selected from the group consisting of nitrogen, carbon monoxide, carbon dioxide, ethene, acetone, water and a combination of two or more thereof, preferably nitrogen. The diluent can, for example, be supplied to the process from the outside. It is equally possible to recycle the diluent within the process by means of one or more recycling steps. It is equally possible to supply a portion of the diluent to the process from the outside, and to recycle a further portion of the diluent within the process by means of one or more recycling steps.

With regard to the ratio between acetic acid and formaldehyde source relative to one or more diluents, stream S4 may in principle have any desired suitable ratio. If nitrogen is the diluent, the proportion in stream S4 is preferably in the range from 0.1% to 80% by volume, further preferably from 0.1% to 70% by volume, further preferably from 0.1% to 60% by volume, further preferably from 0.1% to 50% by volume, further preferably from 0.1% to 20% by volume, further preferably from 0.1% to 10% by volume, further preferably from 0.1% to 5% by volume. If carbon dioxide is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If ethene is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If acetone is the diluent, the proportion in stream S4 is preferably in the range from 0.1% to 50% by volume, further preferably from 0.1% to 20% by volume, further preferably from 0.1% to 10% by volume, further preferably from 0.1% to 5% by volume. If water is the diluent, the proportion in stream S4 is preferably in the range from 0.1% to 40% by volume, further preferably from 0.1% to 35% by volume, further preferably from 0.1% to 30% by volume.

Step (ii)

The Zeolitic Material

According to the present invention, the total content of alkali metal and alkaline earth metal in the zeolitic material in (ii) is from 0% to 0.1% by weight, calculated as alkali metal oxide ($M_2O$) and alkaline earth metal oxide (MO), based on the total weight of the zeolitic material. Consequently, the total content of alkali metal and alkaline earth metal in the zeolitic material in (ii), calculated as alkali metal oxide ($M_2O$) and alkaline earth metal oxide (MO), may in principle assume any value from 0% to 0.1% by weight, based in each case on the total weight of the zeolitic material. Preferably, the zeolitic material in (ii) comprises from 0% to 0.05% by weight, further preferably from 0% to 0.01% by weight, of alkali metal and alkaline earth metal. Further preferably, the total content of alkali metal and alkaline earth metal in the zeolitic material in (ii), calculated as alkali metal oxide ($M_2O$) and alkaline earth metal oxide (MO), is from 0% to 0.005% by weight, further preferably from 0% to 0.001% by weight, further preferably from 0% to 0.0001% by weight, based in each case on the total weight of the zeolitic material. More preferably, the zeolitic material in (ii) is free of alkali metals and alkaline earth metals. "Free of alkali metals and alkaline earth metals" in the context of the present invention means that alkali metals and alkaline earth metals are present only in traces, i.e. in the form of an impurity at most, if at all.

It is further preferable that the aldol condensation catalyst comprises from 0% to 0.1% by weight of alkali metal and alkaline earth metal, calculated as alkali metal oxide ($M_2O$) and alkaline earth metal oxide (MO), based on the total weight of the aldol condensation catalyst. Preferably, the aldol condensation catalyst in (ii) comprises from 0% to 0.05% by weight, further preferably from 0% to 0.01% by weight, of alkali metal and alkaline earth metal. Further preferably, the total content of alkali metal and alkaline earth metal in the aldol condensation catalyst in (ii), calculated as alkali metal oxide ($M_2O$) and alkaline earth metal oxide (MO), is from 0% to 0.005% by weight, further preferably from 0% to 0.001% by weight, further preferably from 0% to 0.0001% by weight, based in each case on the total weight of the aldol condensation catalyst. More preferably, the aldol condensation catalyst in (ii) is free of alkali metals and alkaline earth metals.

The aldol condensation catalyst in (ii) further comprises, outside the framework structure of the zeolitic material present therein, from 0% to 1% by weight of vanadium, calculated as vanadium(V) oxide and based on the total weight of the aldol condensation catalyst. Consequently, the vanadium content of the aldol condensation catalyst in (ii), outside the framework structure of the zeolitic material present therein, may in principle assume any value from 0% to 1% by weight of vanadium, based on vanadium as vanadium(V) oxide. Preferably, the aldol condensation catalyst in (ii) comprises, outside the framework structure of the zeolitic material present therein, from 0% to 0.1% by weight, further preferably from 0% to 0.01% by weight, further preferably from 0% to 0.001% by weight, further preferably from 0% to 0.0001% by weight, of vanadium, calculated as vanadium(V) oxide and based on the total weight of the aldol condensation catalyst. More preferably, the aldol condensation catalyst in (ii), outside the framework structure of the zeolitic material present therein, is free of vanadium. "Free of vanadium" in this context of the present invention likewise means that vanadium is present only in traces, i.e. in the form of an impurity at most, if at all.

In principle, any tetravalent element is an option for the element Y present in the framework structure of the zeolitic material in (ii) present in $YO_2$. Preferably, Y is selected from the group consisting of Si, Sn, Ti, Zr, Ge, V and a combination of two or more thereof. Further preferably, Y is selected from the group consisting of Si, Sn, Ti and a combination of two or more thereof. Further preferably, Y is selected from the group consisting of Si, Sn and a combination of Si and Sn. More preferably, Y is Si.

The framework structure of the zeolitic material in (ii) may, in addition to $Al_2O_3$, comprise the oxide $X_2O_3$ of a trivalent element X other than Al. In principle, all suitable trivalent elements are options here, provided that they can be integrated into the framework structure of the zeolitic material. Preferably, X is selected from the group consisting of B, In, Ga, transition metals of groups 3 to 12, and a combination of two or more thereof. In the context of the present invention, "transition metals of groups 3 to 12" is understood such that lanthanum and the lanthanoids are also included. Therefore, La, Ce, Pr, Nd, Pm, Sm, Eu, Gd, Tb, Dy, Ho, Er, Tm, Yb and Lu are also included. Preferably, X is selected from the group consisting of B, In, Ga, Fe and a combination of two or more thereof.

In principle, the zeolitic material in (ii) is unrestricted in terms of the molar Y:(Al+X) ratio. Preferably, the zeolitic material in (ii) has a molar Y:(Al+X) ratio in the range from 1:1 to 400:1. It is further preferable that the zeolitic material in (ii) has a molar Y:(Al+X) ratio in the range from 1:1 to 300:1, further preferably from 1:1 to 200:1, further preferably from 2:1 to 150:1, further preferably from 3:1 to 100:1. It is further preferable that the zeolitic material in (ii) has a molar Y:(Al+X) ratio in the range from 4:1 to 50:1, further preferably from 6:1 to 35:1, further preferably from 8:1 to 22:1, further preferably from 10:1 to 20:1.

In principle, the zeolitic material in (ii) is unrestricted in terms of the cations which serve to compensate for negative framework charges and are present at the surface and/or in the pores of the zeolitic material in (ii). For example, these cations may be protons $H^+$ or ammonium cations $NH_4^+$. It is preferable that the zeolitic material in (ii) is at least partly in the H form, meaning that at least some of the cations which serve to compensate for negative framework charges are protons. Preferably at least 50% of the cations which serve to compensate for the negative framework charges in the zeolitic material in (ii) are protons, further preferably at least 60%, further preferably at least 70%, further preferably at least 80%, further preferably at least 85%, further preferably at least 90%, further preferably at least 95%, further preferably at least 97%, further preferably at least 98%, further preferably at least 99%, further preferably at least 99.5%, based on the total number of cations which serve to compensate for the negative framework charges in the zeolitic material in (ii). More preferably, the zeolitic material in (ii) is completely in the H form.

If the zeolitic material in (ii) is at least partly in the H form, it is preferable that the framework structure of the zeolitic material in (ii) comprises, optionally in addition to $Al_2O_3$, $X_2O_3$ where X is a trivalent element other than aluminum, and that the molar $NH_4^+$:(Al+X) ratio of the zeolitic material, when it is saturated with $NH_3$, is in the range from 0.01:1 to 1:1. It is further preferable here that the molar $NH_4^+$:(Al+X) ratio of the zeolitic material, when it is saturated with $NH_3$, is in the range from 0.3:1 to 1:1, further preferably from 0.75:1 to 1:1, further preferably from 0.95:1 to 1:1.

In addition, it is possible that the zeolitic material in (ii) comprises at least one non-framework element Z, there being no restriction in principle in accordance with the present invention either in terms of the type or in terms of the amount of non-framework elements which may be present in the zeolitic material. This at least one non-framework element Z is preferably selected from the group consisting of Ti, Zr, Nb, Ta, Cr, Mo, W, Mn, Fe, Co, Ni, Zn, Ga, Ge, In, Sn, Pb, P, N, S and a combination of two or more thereof. Further preferably, the at least one non-framework element Z is selected from the group consisting of P, N, S and a combination of two or more thereof. More preferably, the non-framework element Z is P.

If the at least one non-framework element Z is selected from the group consisting of N, P and S or a combination thereof, it is or they are preferably at least partly in oxidic form. It is especially preferable that N, P and S are present in the form of oxide and/or oxo anion. According to the present invention, an oxide of N, P and S, and especially of P and S, means that the element is bonded to oxygen via one or more covalent bonds, with at least a portion of the element and preferably all the valences of the element covalently bonded to oxygen. The same applies to the oxo anions of N, P and S. With regard to the oxo anions, these may in principle be in the form of the salt and/or in protonated form, it being possible in principle for any suitable cation or combination of cations to be used as salt. According to the present invention, preferred oxo anions of N, P and S are those which are at least partly and preferably fully protonated.

If the non-framework element Z selected is S, it is preferably present in the form of sulfite, sulfate, thiosulfate, dithionite, disulfite, dithionate, disulfate, or in the form of a combination of at least two thereof, further preferably in the form of sulfate and/or disulfate. It is preferably present in the form of sulfate.

If the non-framework element Z selected is P, it is preferably present in the form of $P_4O_6$, $P_2O_4$, $P_4O_{10}$, phosphinate, phosphonate, phosphate, hypodiphosphate, diphosphate and/or polyphosphate, or in the form of a combination of at least two thereof, preferably in the form of phosphate and/or diphosphate, more preferably in the form of phosphate.

In principle, the molar ratio of Al to the at least one non-framework element is unrestricted. Therefore, the molar ratio of Al to the at least one non-framework element may, for example, assume a value within the range from 100:1 to 1:100. Preferably, the molar ratio of Al to the at least one non-framework element is in the range from 10:1 to 1:10, preferably from 5:1 to 1:5. Further preferably, the molar ratio of Al to the at least one non-framework element is in the range from 3:1 to 1:3, further preferably from 2.5:1 to 1:2.5, further preferably from 1.5:1 to 1:1.5.

Zeolites and zeolitic materials, in the context of the present application, are naturally occurring or synthetically produced materials having a three-dimensional structure formed from corner-linked $TO_4$ tetrahedra where T may be any tetrahedrally coordinated cation.

Consequently, for example, options include aluminophosphates (AlPO and APO) and silicoaluminophosphates (SAPO). Aluminophosphates (AlPOs and APOs) in the context of the present invention generally comprise all crystalline aluminophosphate materials. Preferably, the aluminophosphates (AlPOs and APOs) comprise AlPO-20 and variants of various compositions thereof, AlPO-5, AlPO-21, AlPO-H3, AlPO-17 and variants of various compositions thereof, AlPO-12-TAMU, AlPO-11, AlPO-22, AlPO-8, AlPO-C, AlPO-25, AlPO-16, AlPO-31, AlPO-8, AlPO-H2, AlPO-31, AlPO-34, AlPO-D, AlPO-18, AlPO-EN3, AlPO-53(A), AlPO-41, AlPO-52, AlPO4-pollucite, AlPO-24, AlPO-C, AlPO-33, AlPO-17 and variants of various compositions thereof, AlPO-20 and variants of various compositions thereof, AlPO-H2, AlPO-14, AlPO-54, AlPO-53(B), AlPO-40, AlPO-35, AlPO-CJB1 (optionally with additional phosphate groups), AlPO-40, AlPO-36, MnAPO-11, MAPO-43, CoAPO-5, MAPO-36, ZAPO-M1, GaPO-DAB-2, CrAPO-5, CoAPO-50, MAPO-39, CoAPO-44, GaPO-34, MeAPO-47, GaPO-DAB-2, CoAPO-47, MeAPO-47, GaPO-14, CoAPO-50, CFSAPO-1A, GeAPO-11, CoAPO-5, MAPO-5 (where M=Mn), VAPO-5, ZnAPO-5, FAPO-5, MnAPO-41, CoAPO-40, ZnAPO-40, MAPO-46, MnAPO-50, CoAPO-H3, ZnAPO-39, MAPO-31 (where M=Zn, Mn, Co, Cr, Cu, Cd), ZnAPO-36, ZnAPO-35, FAPO-H1, MnAPO-14, ZnAPO-50, APO-CJ3, FAPO-36, MAPO-31 (where M=Mn, Ni, Zn), MAPO-5 (where M=Cd, Cu, Mo, Zr), CoAPO-CJ40 and mixtures of two or more thereof. Further preferably, the aluminophosphates comprise the materials AlPO-5, AlPO-21, AlPO-H3, AlPO-17 and variants of various compositions thereof, AlPO-12-TAMU, AlPO-11, AlPO-22, AlPO-8, AlPO-C, AlPO-25, AlPO-16, AlPO-31, AlPO-8, AlPO-H2, AlPO-31, AlPO-34, AlPO-D, AlPO-18, AlPO-EN3, AlPO-53(A), AlPO-41, AlPO-52, AlPO4-pollucite, AlPO-24, AlPO-C, AlPO-33, AlPO-17 and variants of various compositions thereof, AlPO-20 and variants of various compositions thereof, AlPO-H2, AlPO-14, AlPO-54, AlPO-53(B), AlPO-40, AlPO-35, AlPO-CJB1 (optionally with additional phosphate groups), AlPO-40, AlPO-36, and mixtures of two or more thereof.

Silicoaluminophosphates (SAPOs) in the context of the present invention generally comprise all crystalline aluminosilicophosphate phases, and especially the SAPO materials SAPO-11, SAPO-47, SAPO-40, SAPO-43, SAPO-5, SAPO-31, SAPO-34, SAPO-37, SAPO-35, SAPO-42, SAPO-56, SAPO-18, SAPO-41, SAPO-39 and CFSAPO-1A and mixtures of two or more thereof.

As well as silicoaluminophosphates (SAPOs) and aluminophosphates (AlPOs and APOs), equally useful materials are the zeolitic materials having a three-dimensional framework structure with a structure type selected from the group consisting of ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, SCO, CFI, SGF, CGS, CHA, CHI, CLO, CON, CZP, DAC, DDR, DFO, DFT, DOH, DON, EAB, EDI, EMT, EON, EPI, ERI, ESV, ETR, EUO, FAU, FER, FRA, GIS, GIU, GME, GON, GOO, HEU, IFR, IHW, ISV, ITE, ITH, ITW, IWR, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SOD, SOS, SSY, STF, STI, STT, TER, THO, TON, TSC, UEI, UFI, UOZ, USI, UTL, VET, VFI, VNI, VSV, WIE, WEN, YUG, ZON and mixed structures composed of two or more of these structure types.

For example, the zeolitic material may have, for example, a structure type selected from the group consisting of AEI, AFI, BEA, CDO, CHA, FAU, FER, HEU, LEV, LTL, MEI, MFI, MEL, MOR, MTN, MWW, NON, RRO and a mixed structure composed of two or more of these structure types. Preferably, the zeolitic material in (ii) has a structure type selected from the group consisting of BEA, MFI, MWW, FAU, MEL, MTN, RRO, CDO, LTL, MOR, AFI, FER, LEV and a mixed structure composed of two or more of these structure types. Further preferably, the zeolitic material in (ii) has a structure type selected from the group consisting of BEA, MFI, MWW, FAU and a mixed structure composed of two or more of these structure types. More preferably, the zeolitic material in (ii) has the BEA structure type.

In particularly preferred embodiments of the present invention in which the zeolitic material has the BEA structure type, it is further preferable that the zeolitic material is at least partly in the H form, in which case preferably from 50% to 100% of the cations which serve to compensate for the negative framework charges in the zeolitic material in (ii), further preferably from 60% to 100%, further preferably from 70% to 100%, further preferably from 80% to 100%, further preferably from 85% to 100%, further preferably from 90% to 100%, further preferably from 95% to 100%, further preferably from 97% to 100%, further preferably from 98% to 100%, further preferably from 99% to 100%, further preferably from 99.5% to 100%, are protons, based on the total number of cations. More preferably, the zeolitic material having the BEA structure type is completely in the H form.

In particularly preferred embodiments of the present invention in which the zeolitic material has the BEA structure type, and especially in particularly preferred embodiments in which the zeolitic material of the BEA structure type is at least partly and further preferably completely in the H form, it is further preferable that the zeolitic material comprises at least one non-framework element Z, preferably selected from the group consisting of Ti, Zr, Nb, Ta, Cr, Mo, W, Mn, Fe, Co, Ni, Zn, Ga, Ge, In, Sn, Pb, P, N, S and a combination of two or more thereof. Further preferably, the at least one non-framework element Z is selected from the group consisting of P, N, S and a combination of two or more thereof. More preferably, in these preferred embodiments of the present invention, the zeolitic material of the BEA structure type, which is at least partly and preferably completely in the H form, comprises P as non-framework element Z, where P is preferably present in the form of oxide and/or oxo anion, further preferably as phosphate, and the phosphate is further preferably at least partly and preferably completely in protonated form.

If the zeolitic material in (ii) is an SAPO material or an APO material, the zeolitic material is fully unrestricted in general terms with regard to the structure type. If the zeolitic material in (ii) is an SAPO material or an APO material, however, it is preferable that the zeolitic material in (ii) has a structure type selected from the group consisting of AEL, CHA, AFR, GIS, AFI, ATO, FAU, LEV, LTA, AFX, AEN, AEI, AFO, ATN, AVL, AFV, mixed structures composed of two or more of these structure types, and a combination of two or more thereof, preferably AEL.

With regard to the aldol condensation catalyst used in the process according to the invention, there is in principle no restriction whatsoever with regard to the constituents present therein, provided that it comprises a zeolitic material, where the framework structure of the zeolitic material in (ii) comprises $YO_2$ and $Al_2O_3$ and Y is a tetravalent element, where the total content of alkali metal and alkaline earth metal in the zeolitic material in (ii), calculated as alkali metal oxide ($M_2O$) and alkaline earth metal oxide (MO), is from 0% to 0.1% by weight, and where the aldol condensation catalyst comprises, outside the framework structure of the zeolitic material present therein, from 0% to 0.0001% by weight of vanadium. It is thus possible in principle that the aldol condensation catalyst in (ii) also comprises vanadium in the framework structure of the zeolitic material present therein. It is preferable that the aldol condensation catalyst in (ii) comprises a total of from 0% to 1% by weight of vanadium, calculated as vanadium(V) oxide and based on the total weight of the aldol condensation catalyst. Preferably, the aldol condensation catalyst in (ii) comprises a total of from 0% to 0.1% by weight, further preferably from 0% to 0.01% by weight, further preferably from 0% to 0.001% by weight, further preferably from 0% to 0.0001% by weight, of vanadium, based on vanadium as vanadium(V) oxide. More preferably, the aldol condensation catalyst in (ii) is totally free of vanadium. "Free of vanadium" in this context of the present invention means that vanadium is present only in traces, i.e. in the form of an impurity at most, if at all.

Therefore, the zeolitic material used in the aldol condensation catalyst is not restricted in principle, for example, with regard to its acid-base properties, provided that the reaction of the formaldehyde source with acetic acid to give acrylic acid can be at least partly assured. According to the present invention, the zeolitic material, however, preferably has acid sites, these comprising Brønsted and/or Lewis acid sites. Accordingly, the zeolitic material preferably has one or more desorption maxima in its desorption spectrum obtained by temperature-programmed desorption with $NH_3$ ($NH_3$-TPD).

It is preferable that the zeolitic material in (ii) has a desorption maximum within at least one of the temperature ranges of 0 to 250° C., 251 to 500° C. and 501 to 700° C. in a temperature-programmed desorption with $NH_3$. It is therefore preferable that the zeolitic material in (ii) has a desorption maximum within the temperature range of 0 to 250° C. and/or within the temperature range of 251 to 500° C. and/or within the temperature range of 501 to 700° C.

With regard to the intensity of the one or more desorption maxima preferably present in the desorption spectrum of the zeolitic material obtained by $NH_3$-TPD, there are no restrictions at all in principle, and so the relative amount of acidic sites in the zeolitic material is not subject to any restrictions in principle. According to the present invention, it is preferable that, after deconvolution of the desorption spectrum, the desorption maximum within the temperature range of 0 to 250° C. has a concentration of desorbed $NH_3$ in the range from 0.05 to 2.0 mmol/g and/or the desorption maximum within the temperature range of 251 to 500° C. has a concentration of desorbed $NH_3$ in the range from 0.05 to 1.5 mmol/g and/or the desorption maximum within the temperature range of 501 to 700° C. has a concentration of desorbed $NH_3$ in the range from 0.001 to 0.5 mmol/g, where the concentration of desorbed $NH_3$ in mmol is based on the mass of the zeolitic material in g.

Further preferably, after deconvolution of the desorption spectrum, the desorption maximum within the temperature range of 0 to 250° C. has a concentration of desorbed $NH_3$ in the range from 0.1 to 1.5 mmol/g, further preferably in the range from 0.25 to 1.25 mmol/g, further preferably in the range from 0.3 to 1.0 mmol/g. Equally preferably, after deconvolution of the desorption spectrum, the desorption maximum within the temperature range of 251 to 500° C. has a concentration of desorbed $NH_3$ in the range from 0.075 to 1.25 mmol/g, further preferably in the range from 0.1 to 1.0 mmol/g, further preferably in the range from 0.15 to 0.4 mmol/g. Likewise further preferably, after deconvolution of the desorption spectrum, the desorption maximum within the temperature range of 501 to 700° C. has a concentration of desorbed $NH_3$ in the range from 0.005 to 0.1 mmol/g, further preferably from 0.0075 to 0.05 mmol/g, further preferably from 0.01 to 0.03 mmol/g.

Independently of this, the zeolitic material present in the aldol condensation catalyst is preferably characterized by its IR spectrum. More particularly, this preferably has at least one maximum of an absorption band in the range from 3790 to 3691 $cm^{-1}$ and/or in the range from 3690 to 3591 $cm^{-1}$ and/or in the range from 3590 to 3490 $cm^{-1}$. Further preferably, it has at least one maximum of an absorption band in the range from 3790 to 3691 $cm^{-1}$ and/or in the range from 3690 to 3591 $cm^{-1}$.

Finally, the zeolitic material present in the aldol condensation catalyst, independently of this, is preferably characterized by its hydrophilic/hydrophobic properties, which are reflected in its ability to absorb water. More particularly, the zeolitic material preferably features a water absorption in the range from 1% to 50% by weight, preferably in the range from 10% to 25% by weight. In the context of the present invention, the water absorption is based on the relative amount of water which is absorbed by the zeolitic material, proceeding from its dry weight up to a relative humidity of the ambient air of 85% at 25° C. According to the present invention, the water absorption measured for the zeolitic material is preferably based on the process for determination thereof described in the experimental section.

It is additionally preferable that the aldol condensation catalyst in (ii) comprises a binder material in addition to the zeolitic material in (ii). Possible binder materials include all the materials which are known to those skilled in the art and can be used here as binder material, and which affect the catalyst only to a minor degree or only to the degree of the resulting dilution of the catalyst, if at all.

Preferably, the binder material is selected from the group consisting of graphite, $SiO_2$, $TiO_2$, $ZrO_2$, combinations of two or more thereof and mixed oxides of at least two elements selected from the group consisting of Si, Ti, Zr and combinations of two or more thereof. The ratio of the zeolitic material in (ii) to the binder material is not subject to any restrictions in principle. In general, the weight ratio of the zeolitic material in (ii) to the binder material is in the range from 20:1 to 1:20, preferably from 10:1 to 1:10, further preferably from 1:1 to 1:10.

The aldol condensation catalyst in (ii) may, as well as the zeolitic material in (ii) and the binder material, also comprise further components, possible options here being supports or else, as well as the zeolitic material, further catalytically active components. Therefore, the aldol condensation catalyst in (ii) preferably consists of zeolitic material and any binder material to an extent of 30% to 100% by weight, further preferably to an extent of 50% to 100% by weight, further preferably to an extent of 70% to 100% by weight, further preferably to an extent of 80% to 100% by weight, further preferably to an extent of 90% to 100% by weight, further preferably to an extent of 95% to 100% by weight, further preferably to an extent of 98% to 100% by weight, further preferably to an extent of 99% to 100% by weight.

The aldol condensation catalyst in (ii) may be in any form suitable for the performance of the process according to the invention. Consequently, the aldol condensation catalyst in (ii) may be in powder form, in the form of spray powder, or in the form of spray granules. Equally, the aldol condensation catalyst may be in the form of shaped bodies. If the aldol condensation catalyst is in the form of shaped bodies, it is preferably shaped to extrudates, preferably having a rectangular, triangular, hexagonal, square, oval or circular cross section, or is in a star shape, in tablet form, in the form of spheres, or in the form of hollow cylinders. Equally possible is a combination of two or more of the aforementioned forms.

Process Parameters

In step (ii) of the process according to the invention, stream S4 is contacted with an aldol condensation catalyst comprising a zeolitic material to obtain stream S6 comprising acrylic acid. Stream S4 may be present here completely in gaseous form, completely in liquid form or in such a form that at least one component is in gaseous form and at least one component is in liquid form. Preferably, stream S4 in step (ii) is completely in gaseous form.

In principle, the present process can be conducted at all temperatures at which a stream S6 comprising acrylic acid is obtained with the aid of the process comprising steps (i) and (ii). Preferably, the contacting in (ii) of the process according to the invention is effected at a temperature in the range from 200 to 400° C., further preferably from 220 to 380° C. Further preferably, the contacting in (ii) is effected at a temperature in the range from 230 to 370° C., further preferably from 240 to 360° C., further preferably from 250 to 350° C. This temperature should be understood as the highest temperature of the gas phase in the reactor used for the reaction in (ii), measured with an unprotected Pt-100 thermocouple.

In principle, the present process can be conducted at all pressures at which a stream S6 comprising acrylic acid is obtained with the aid of the process comprising steps (i) and (ii). Preferably, the contacting in (ii) is effected at a pressure in the range from 0.01 to 10 bar, further preferably from 0.02 to 7.5 bar, further preferably from 0.05 to 5 bar. Further preferably, the contacting in (ii) is effected at a pressure in the range from 0.1 to 3.5 bar, further preferably from 0.5 to 2.5 bar, further preferably from 0.75 to 2.0 bar, further preferably from 0.9 to 1.5 bar. All pressures in the context of the present invention should be understood as absolute pressures.

Preferably, the contacting in (ii) of the process according to the invention is effected at a temperature in the range from 200 to 400° C., further preferably from 220 to 380° C., further preferably from 230 to 370° C., further preferably from 240 to 360° C., further preferably from 250 to 350° C., and a pressure of 0.01 to 10 bar, further preferably of 0.02 to 7.5 bar, further preferably of 0.05 to 5 bar, further preferably of 0.1 to 3.5 bar, further preferably of 0.5 to 2.5 bar, further preferably of 0.75 to 2.0 bar, further preferably of 0.9 to 1.5 bar. Preferably, the contacting in (ii) of the process according to the invention is effected at a temperature in the range from 200 to 400° C. and a pressure of 0.01 to 10 bar, more preferably at a temperature in the range from 250 to 350° C. and a pressure of 0.5 to 2.5 bar.

The space velocity (gas hourly space velocity, GHSV) with respect to the contacting in (ii) of the process according to the invention is preferably chosen such that a satisfactory balance of conversion, selectivity, yield, reactor geometry, reactor dimensions and process regime is obtained. In the context of the present invention, the space velocity is understood to mean the ratio of the volume flow rate S4 in [volume/time] to the three-dimensional volume of the aldol condensation catalyst in (ii) in [volume] and therefore has the unit [1/time]. Preferably, the space velocity in the present process is in the range from 50 to 10 000 $h^{-1}$, preferably from 70 to 7500 $h^{-1}$, further preferably from 90 to 5000 $h^{-1}$, further preferably from 100 to 2500 $h^{-1}$, further preferably from 150 to 2000 $h^{-1}$, in each case at a pressure of 101,325 kPa and a temperature of 0° C.

A further important process parameter in the context of the present invention is the space-time yield (STY). In the context of the present invention, the space-time yield is understood to mean the ratio of the mass flow rate of acrylic acid in stream S6 with the unit (mass/time) to the mass of the aldol condensation catalyst in (ii); the space-time yield therefore has the unit (mass/mass/time). Preferably, the space-time yield in the present process is in the range from 0.01 to 2.5 kg/kg/h, further preferably from 0.025 to 2.0 kg/kg/h, further preferably 0.05 to 1.75 kg/kg/h, further preferably from 0.05 to 1.0 kg/kg/h.

Further Steps

The process according to the invention may of course comprise further steps in addition to steps (i) and (ii). Therefore, the process according to the invention preferably additionally comprises, as step (iii), the regenerating of the aldol condensation catalyst in (ii).

The regenerating in (iii) is preferably conducted at a temperature in the range from 300 to 700° C., further preferably from 350 to 600° C. The regenerating in (iii) is preferably conducted over a period of 1 to 48 hours, further preferably of 10 to 40 hours, further preferably of 20 to 30 hours, further preferably of 22 to 26 hours. The regenerating in (iii) is preferably conducted in the presence of oxygen. Therefore, the regenerating in (ii) can be conducted in the presence of pure oxygen or else in the presence of a gas mixture comprising oxygen. It is preferable that the regenerating in (iii) is conducted in the presence of a gas mixture of oxygen and an inert gas, the inert gas preferably being nitrogen. Therefore, the regenerating in (iii) is preferably conducted in the presence of a gas mixture of oxygen and nitrogen. Therefore, step (iii) is preferably conducted at a temperature in the range from 350 to 600° C. in the presence of a gas mixture of oxygen and nitrogen.

The space velocity (gas hourly space velocity, GHSV) with respect to the regenerating in (iii) of the process according to the invention may assume any value at which regeneration of the aldol condensation catalyst in (ii) is achieved. Preferably, the space velocity with respect to the regenerating is in the range from 50 to 10 000 $h^{-1}$, preferably from 100 to 7500 $h^{-1}$, further preferably from 75 to 5000 $h^{-1}$, further preferably from 100 to 2500 $h^{-1}$.

The present invention is illustrated in detail by the following embodiments and combinations of the embodiments which are apparent from the dependency references and other references:

1. A process for preparing acrylic acid, comprising
   (i) providing a stream S4 comprising a formaldehyde source and acetic acid;
   (ii) contacting stream S4 with an aldol condensation catalyst comprising a zeolitic material comprising aluminum in the framework structure to obtain a stream S6 comprising acrylic acid, the framework structure of the zeolitic material in (ii) comprising $YO_2$ and $Al_2O_3$, and Y being a tetravalent element;

where the total content of alkali metal and alkaline earth metal in the zeolitic material in (ii), calculated as alkali metal oxide ($M_2O$) and alkaline earth metal oxide (MO), is from 0% to 0.1% by weight, preferably from 0% to 0.05% by weight, further preferably from 0% to 0.01% by weight, further preferably from 0% to 0.001% by weight, based in each case on the total weight of the zeolitic material, and where the aldol condensation catalyst in (ii) comprises, outside the framework structure of the zeolitic material present in the aldol condensation catalyst, from 0% to 1% by weight, preferably from 0% to 0.1% by weight, further preferably from 0% to 0.01% by weight, further preferably from 0% to 0.001% by weight, further preferably from 0% to 0.0001% by weight, of vanadium, calculated as vanadium(V) oxide and based on the total weight of the aldol condensation catalyst.

2. The process according to embodiment 1, wherein the zeolitic material in (ii) is an SAPO material or an APO material.

3. The process according to embodiment 1 or 2, wherein Y is selected from the group consisting of Si, Sn, Ti, Zr, Ge, V and a combination of two or more thereof, preferably from the group consisting of Si, Sn, Ti and a combination of two or more thereof, further preferably from the group consisting of Si, Sn and a combination thereof.

4. The process according to any of embodiments 1 to 3, wherein the framework structure of the zeolitic material in (ii), in addition to $Al_2O_3$, comprises $X_2O_3$ where X is a trivalent element other than aluminum and where X is preferably selected from the group consisting of B, In, Ga, transition metals of groups 3 to 12 and a combination of two or more thereof, further preferably selected from the group consisting of B, In, Ga, Fe and a combination of two or more thereof.

5. The process according to embodiment 4, wherein the zeolitic material in (ii) has a molar Y:(Al+X) ratio in the range from 1:1 to 400:1, preferably from 2:1 to 150:1, further preferably from 3:1 to 100:1, further preferably from 4:1 to 50:1, further preferably from 6:1 to 35:1, further preferably from 8:1 to 22:1, further preferably from 10:1 to 20:1.

6. The process according to any of embodiments 1 to 5, wherein the zeolitic material in (ii) is at least partly in the H form.

7. The process according to embodiment 6, wherein the framework structure of the zeolitic material in (ii) comprises, optionally in addition to $Al_2O_3$, $X_2O_3$ where X is a trivalent element other than aluminum, where the molar $NH_4+$:(Al+X) ratio of the zeolitic material, when it is saturated with $NH_3$, is in the range from 0.01:1 to 1:1, preferably from 0.3:1 to 1:1, further preferably from 0.75:1 to 1:1, further preferably from 0.95:1 to 1:1.

8. The process according to any of embodiments 1 to 7, wherein the zeolitic material in (ii) comprises at least one non-framework element Z, preferably selected from the group consisting of Ti, Zr, Nb, Ta, Cr, Mo, W, Mn, Fe, Co, Ni, Zn, Ga, Ge, In, Sn, Pb, P, N, S and a combination of two or more thereof, further preferably consisting of P, N, S and a combination of two or more thereof, further preferably P.

9. The process according to embodiment 8, wherein N, P and S are present at least partly in oxidic form, preferably as oxide and/or oxo anion.

10. The process according to embodiment 8 or 9, wherein the molar ratio of Al to the at least one non-framework element is in the range from 10:1 to 1:10, preferably from 5:1 to 1:5, further preferably from 3:1 to 1:3, further preferably from 1.5:1 to 1:1.5.

11. The process according to any of embodiments 1 to 10, wherein the zeolitic material in (ii) has a structure type selected from the group consisting of BEA, MFI, MWW, FAU, MEL, MTN, RRO, CDO, LTL, MOR, AFI, FER, LEV and a mixed structure composed of two or more of these structure types, preferably BEA.

12. The process according to any of embodiments 1 to 10, wherein the zeolitic material in (ii) is an SAPO material or an APO material and has a structure type selected from the group consisting of AEL, CHA, AFR, GIS, AFI, ATO, FAU, LEV, LTA, AFX, AEN, AEI, AFO, ATN, AVL, AFV and a mixed structure composed of two or more of these structure types, preferably AEL.

13. The process according to any of embodiments 1 to 12, wherein the aldol condensation catalyst in (ii) comprises a binder material in addition to the zeolitic material.

14. The process according to embodiment 13, wherein the binder material is selected from the group consisting of graphite, $SiO_2$, $TiO_2$, $ZrO_2$, mixtures of two or more thereof, mixed oxides of at least two elements selected from the group consisting of Si, Ti, Zr, and mixtures of two or more thereof.

15. The process according to any of embodiments 1 to 14, wherein the aldol condensation catalyst is in the form of shaped bodies, preferably shaped to extrudates, preferably having a rectangular, triangular, hexagonal, square, oval or circular cross section, or is in a star shape, in tablet form, in the form of spheres, or in the form of hollow cylinders.

16. The process according to any of embodiments 1 to 15, wherein the molar ratio of acetic acid to formaldehyde, obtained or obtainable from the formaldehyde source, in stream S4 is in the range from 0.01:1 to 10:1, preferably from 1:1 to 8:1, preferably from 1.5:1 to 5:1, further preferably from 2:1 to 4.4:1, further preferably from 2.5:1 to 4.1:1.

17. The process according to any of embodiments to 16, wherein stream S4 is brought to a temperature in the range from 150 to 250° C., preferably 180 to 220° C., before being contacted in (ii).

18. The process according to any of embodiments 1 to 17, wherein the contacting in (ii) is effected at a temperature in the range from 200 to 400° C., preferably from 230 to 370° C., further preferably from 250 to 350° C.

19. The process according to any of embodiments 1 to 18, wherein the contacting in (ii) is effected at a pressure in the range from 0.01 to 10 bar, preferably from 0.05 to 5 bar, preferably from 0.1 to 3.5 bar, further preferably from 0.5 to 2.5 bar.

20. The process according to any of embodiments 1 to 19, wherein the contacting in (ii) is effected at a space velocity (gas hourly space velocity, GHSV) in the range from 50 to 10 000 $h^{-1}$, preferably from 70 to 7500 $h^{-1}$, further preferably from 90 to 5000 $h^{-1}$, further preferably from 100 to 2500 $h^{-1}$, further preferably from 150 to 2000 $h^{-1}$.

21. The process according to any of embodiments 1 to 20, wherein the space-time yield in the contacting in (ii) is in the range from 0.01 to 2.5 kg/kg/h, preferably from 0.025 to 2.0 kg/kg/h, further preferably 0.05 to 1.75 kg/kg/h, the space-time yield being defined as kg(acrylic acid)/kg (aldol condensation catalyst)/h.

22. The process according to any of embodiments 1 to 21, wherein stream S4 additionally comprises one or more diluents, preferably selected from the group consisting of nitrogen, carbon monoxide, carbon dioxide, ethene, acetone, water and a combination of two or more thereof.
23. The process according to any of embodiments 1 to 22, additionally comprising
    (iii) regenerating the aldol condensation catalyst in (ii), the regenerating preferably being conducted at a temperature from 300 to 700° C., further preferably from 350 to 600° C., the regenerating preferably being conducted in the presence of oxygen, further preferably in the presence of a mixture of oxygen and an inert gas, further preferably in the presence of a mixture of oxygen and nitrogen.
24. The process according to any of embodiments 1 to 23, wherein the formaldehyde source is an anhydrous formaldehyde source, preferably selected from the group consisting of trioxane and paraformaldehyde.
25. The process according to any of embodiments 1 to 24, wherein the temperature-programmed desorption with $NH_3$ ($NH_3$-TPD) of the zeolitic material in (ii) has a desorption maximum within at least one of the temperature ranges of 0 to 250° C., 251 to 500° C. and 501 to 700° C., wherein following deconvolution of the desorption spectrum the desorption maximum in the temperature range of 0 to 250° C. has a concentration of desorbed $NH_3$ in the range from 0.05 to 2.0 mmol/g, the desorption maximum in the temperature range of 251 to 500° C. a concentration of desorbed $NH_3$ in the range from 0.05 to 1.5 mmol/g, and the desorption maximum in the temperature range 501 to 700° C. a concentration of desorbed $NH_3$ in the range from 0.001 to 0.5 mmol/g, where the concentration of desorbed $NH_3$ is defined as mmol(desorbed $NH_3$)/g(zeolitic material).
26. The process according to any of embodiments 1 to 25, wherein the IR spectrum of the zeolitic material in (ii) has at least one maximum of an absorption band within at least one of the wavelength ranges of 3790 to 3691 $cm^{-1}$, 3690 to 3591 $cm^{-1}$ and 3590 to 3490 $cm^{-1}$.
27. The process according to any of embodiments 1 to 26, wherein the zeolitic material in (ii) has a water absorption in the range from 1% to 50% by weight, preferably in the range from 10% to 25% by weight.
28. The process according to any of embodiments 1 to 27, wherein the aldol condensation catalyst in (ii) comprises not more than 1% by weight, preferably not more than 0.1% by weight, further preferably not more than 0.01% by weight, further preferably not more than 0.001% by weight, further preferably not more than 0.0001% by weight, of vanadium, calculated as vanadium(V) oxide and based on the total weight of the aldol condensation catalyst.

DESCRIPTION OF THE FIGURE

FIG. 1 shows the temperature-programmed desorption ($NH_3$-TPD) which was obtained for the zeolitic material according to example 3. Plotted on the abscissa is the temperature in ° C., with explicitly stated values, from left to right, of 100; 150; 200; 250; 300; 350; 400; 450; 500; 550 and 600, and on the ordinate the concentration of the desorbed $NH_3$, measured by means of a thermal conductivity detector, with explicitly stated values, from the bottom upward, of 0.8; 0.9; 1.0; 1.1; 1.2; 1.3 and 1.4. On the curve itself, from left to right, the temperature values, in ° C., of 212.5 (maximum); 326.1 (shoulder) and 601.4 (last value).

The present invention will now be illustrated further by the examples and comparative examples which follow.

EXAMPLES

I. Analytical Methods

I.1 $NH_3$-TPD

The temperature-programmed desorption of ammonia ($NH_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analyzed using the program described below. The temperature was measured by means of an Ni/Cr/Ni thermocouple immediately above the sample in the quartz tube. For the analyses, He of purity 5.0 was used. Before any measurement, a blank sample was analyzed for calibration.

1. Preparation
    Commencement of recording; one measurement per second.
    Wait for 10 minutes at 25° C. and a He flow rate of 30 $cm^3$/min (room temperature (about 25° C.) and 1 atm); heat up to 600° C. at a heating rate of 20 K/min; hold for 10 minutes.
    Cool down under a He flow (30 $cm^3$/min) to 100° C. at a cooling rate of 20 K/min (furnace ramp temperature);
    Cool down under a He flow (30 $cm^3$/min) to 100° C. at a cooling rate of 3 K/min (sample ramp temperature).
2. Saturation with $NH_3$
    Commencement of recording; one measurement per second.
    Change the gas flow to a mixture of 10% $NH_3$ in He (75 $cm^3$/min; 100° C. and 1 atm) at 100° C.; hold for 30 minutes.
3. Removal of the excess
    Commencement of recording; one measurement per second.
    Change the gas flow to a He flow of 75 $cm^3$/min (100° C. and 1 atm) at 100° C.; hold for 60 minutes.
4. $NH_3$-TPD
    Commencement of recording; one measurement per second.
    Heat up under a He flow (flow rate: 30 $cm^3$/min) to 600° C. at a heating rate of 10 K/min; hold for 30 minutes.
5. End of measurement Desorbed ammonia was measured by means of the online mass spectrometer, which demonstrates that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

I.2 Gas Chromatography

The analysis of the gaseous product stream was conducted by means of an online GC-MS system from Agilent. The instrument was equipped with a 10-way valve having two sample loops (500 microliters/1000 microliters) which were operated at 220° C. The detection was effected with the aid of a flame ionization detector (FID) and two thermal conductivity detectors. For the FID flow rate supplied through the front inlet, the following parameters were chosen: injector temperature: 275° C.; split: 1:5. An FFAP column having length 30 m, internal diameter 0.32 mm and film thickness 0.5 micrometer (column flow rate: 5 mL/min) was used. The thermal conductivity detectors were supplied with the sample through the rear inlet in parallel by means of a Y adapter (JAS). Here, the following parameters were chosen: injector temperature: 275° C.; split: 1:2. For the first thermal conductivity detector, a column of the Volamine type having a length of 60 m, an internal diameter of 0.32 mm and a film thickness of 0.45 micrometer (column flow rate: 2 mL/min) was used. The second thermal conductivity detector had a column system with two columns. First column: RTX5 having a length of 30 m, an internal diameter of 0.32 mm, a film thickness of 1 micrometer (column flow rate: 5 mL/min). Second column: "select permanent gases/$CO_2$ HR" having a length of 50 m, an internal diameter of 0.32 mm, a film thickness of 10 micrometers (column flow rate: 2 mL/min). All columns were operated with helium as carrier gas. The GC oven temperature program was as follows:

40° C. (hold time 2.5 min)
heating to 105° C. at a heating rate of 20 K/min (hold time 0 min)
heating to 225° C. at a heating rate of 40 K/min (hold time 2.75 min)

I.3 FTIR Spectroscopy

The IR measurements were effected on a Nicolet 6700 spectrometer. The zeolitic material was compressed to a pellet without the addition of additives. The pellet was introduced into the high-vacuum cell of the IR spectrometer. Before the measurement, the sample was pretreated under high vacuum ($10^{-5}$ mbar) at 300° C. for 3 h. The spectra were recorded after the cell had been cooled down to 50° C. The spectra were recorded within a range from 4000 $cm^{-1}$ to 800 $cm^{-1}$ at a resolution of 2 $cm^{-1}$. The spectra obtained were shown by a plot with the wavelength on the abscissa and the absorption (in arbitrary units) on the ordinate. For quantitative evaluation of the signal intensities and the ratio of the signals, a baseline correction was undertaken.

I.4 Water absorption

The isotherms with respect to the water adsorption/desorption were measured on a VTI SA instrument from TA Instruments. The experiment consisted of one pass or a series of passes of a sample which was introduced into the weighing pan of the microbalance within the instrument. Prior to the measurement, the residual moisture was removed from the sample by heating to 100° C. (heating rate 5 K/min) and holding it at this temperature in a nitrogen stream for 6 h. After drying, the temperature in the cell was lowered to 25° C. and kept isothermal during the measurements. The microbalance was calibrated, and the weight of the dried sample served as reference value (maximum deviation in mass: 0.01% by weight). The water absorption of the sample was determined from its increase in weight compared to the dry sample. First of all, an adsorption curve was recorded with increasing relative humidity (RH; in % by weight of water in the atmosphere within the measurement cell) to which the sample was exposed, and the water absorption of the sample was measured at equilibrium. The relative humidity was increased in steps of 10 percentage points by weight from 5% to 85%. In each step, the system checked the relative humidity, recorded the weight of the sample until attainment of equilibrium conditions, and also recorded the water absorption. The total amount of water that the sample absorbed was determined by exposing the sample to a relative humidity of 85% by weight. During the desorption measurement, the relative humidity was reduced in steps of 10 percentage points from 85% by weight to 5% by weight. The change in weight of the sample (water absorption) was monitored and recorded.

II. Production of the Zeolitic Materials

II.1 Example 1

30.01 g of zeolitic material (CP814E, from Zeolyst; $NH_4^+$ form; $Na_2O$: 0.05% by weight) were mixed with 0.928 g of graphite and tableted (Korsch XP1, 13 mm die, upper setting wheel: 6.5 mm, lower setting wheel: 7.0 mm, 15 kN; resulting tablet height: 1 mm). Then the tableted mixture was comminuted, so as to obtain a powder having a particle diameter in the range from 0.315 mm to 0.500 mm. The material obtained was brought to 500° C. (heating rate 1 K/min) and converted to the H form at 500° C. in a nitrogen stream (0.4 L/min) for 2 h.

II.2 Example 2

29.15 g of zeolitic material (CP814C, from Zeolyst, $NH_4^+$ form; $Na_2O$: 0.05% by weight) were mixed with 0.901 g of graphite and tableted (Korsch XP1, 13 mm die, upper setting wheel: 6.5 mm, lower setting wheel: 7.0 mm, 15 kN; resulting tablet height: 1 mm). Then the tableted mixture was comminuted, so as to obtain a powder having a particle diameter in the range from 0.315 mm to 0.500 mm. The material obtained was brought to 500° C. (heating rate 1 K/min) and converted to the H form at 500° C. in a nitrogen stream (0.4 L/min) for 2 h.

II.3 Example 3

The material obtained from example II.2 was mixed with 3% by weight of graphite and tableted (Korsch XP1, 13 mm die, 35 kN). Then the tableted mixture was comminuted, so as to obtain a powder having a particle diameter in the range from 0.315 mm to 0.500 mm.

Subsequently, water absorption of the material thus obtained was determined by stepwise addition of small portions of water until attainment of the maximum amount of water absorbable by the material.

Based on the water absorption of the material thus determined, an aqueous $(NH_4)H_2(PO_4)$ impregnating solution was prepared; the concentration and amount of the impregnating solution were chosen such that, in the subsequent contacting with the tableted and comminuted material, assuming complete absorption of the impregnating solution by the material, a P content of 4.2% by weight, based on the resulting material, was obtained.

The tableted and comminuted material and the impregnating solution described were contacted with one another, so as to obtain, for the material, a P content of 4.2% by weight, based on the resulting material.

The material thus obtained was aged under air at room temperature for 30 min and then blanketed with liquid nitrogen. The material thus shock-frozen was dried at −10° C. and 2.56 mbar for 16 h. Subsequently, the material was brought to 500° C. (heating rate 1 K/min) and calcined at 500° C. under air for 2 h.

II.4 Comparative Examples

In addition, the following commercially available zeolitic materials were used:

TABLE 1

Materials used in the comparative examples, corresponding manufacturers, product name, molar $SiO_2:Al_2O_3$ ratio and $Na_2O$ content in % by weight

| Comparative example | Manufacturer | Product name | Molar ratio $SiO_2:Al_2O_3$ | $Na_2O$ content/ % by weight |
|---|---|---|---|---|
| C1 | Zeochem ® | ZEOcat ® PB (Na-Beta) | 20 | 0.6 |
| C2 | Zeochem ® | ZEOcat ® PZ 2/400 (Na-ZSM-5) | 400 | 0.7 |
| C3 | Zeochem ® | ZEOcat ® FM-8 (Na-Mor) | 12 | 6.8 |
| C4 | Zeolyst ® | $NH_4$-MFI 30 (CBV3024E) | 30 | 0.05 |

III. Catalytic Studies

A stream consisting of trioxane (6.3% by volume; Sigma-Aldrich, 1,3,5-trioxane, 99%), acetic acid (83.7% by volume; PanReac AppliChem, acetic acid 100% for analysis C, A0820) and argon (10% by volume; 5.0 purity) was heated to 200° C. and hence evaporated (acetic acid:formaldehyde equivalents=4.4:1).

The gaseous mixture was then contacted with a pulverulent aldol condensation catalyst according to examples 1 to 3 and the comparative examples at 260 or 290° C. and 1.1 bar (GHSV: 200 $h^{-1}$).

The temperature was measured at the start of the experiment by means of a thermocouple in the isothermal zone of the reactor, i.e. of the catalyst bed, and corresponds to the temperature at which the reactions were conducted. The product stream was subsequently diluted with nitrogen (purity: 5.0) ($N_2$: product stream=22:1), and the composition was determined by gas chromatography.

The data shown below show the averaged result, the process according to the invention having been conducted for 6 h. Tables 2 and 3 show the results of the process according to the invention; tables 4 and 5 show the analogous data, with use here of the commercially available zeolitic materials detailed under 11.2 as aldol condensation catalyst.

The analytical data for the zeolitic materials according to examples 1 to 3 are shown in table 6.

TABLE 2

Catalytic results of the inventive examples at a temperature of 290° C.

| Zeolitic material according to ex. | Carbon conversion/ %[2] | AA yield/ %[3] | AA selectivity/ %[4] | STY/ kg/kg(cat.)/ h[5] |
|---|---|---|---|---|
| 1 | 9.06 | 7.09 | 78.39 | 0.0965 |
| 1b[1] | 10.10 | 8.25 | 81.60 | 0.1498 |
| 2 | 9.66 | 7.59 | 78.47 | 0.0794 |
| 3 | 9.27 | 8.05 | 86.24 | 0.0795 |

[1]Zeolitic material was produced as described in II and used directly; samples without addition of "b" were first subjected to an experiment at 260° C. (cf. table 2), regenerated under air at 350° C. for 24 h (10% by volume of argon, 2% by volume of oxygen, 88% by volume of nitrogen; GHSV: 2000 $h^{-1}$) and then used at 290° C.

TABLE 2-continued

Catalytic results of the inventive examples at a temperature of 290° C.

| Zeolitic material according to ex. | Carbon conversion/ %[2] | AA yield/ %[3] | AA selectivity/ %[4] | STY/ kg/kg(cat.)/ h[5] |
|---|---|---|---|---|

[2]The carbon conversion (C) is calculated by the following equation:

$C = 100 * (NC^P_{sum}/(NC^E_{FA} + NC^E_{ES}))$ $NC^P_{sum} = (NC^E_{FA} + NC^E_{ES}) - (NC^P_{FA} + NC^P_{ES})$;

$NC^E_{FA}$ = number of carbon atoms present in stream S4 in the form of a formaldehyde source;

$NC^E_{ES}$ = number of carbon atoms present in stream S4 in the form of acetic acid;

$NC^P_{FA}$ = number of carbon atoms present in product stream S6 in the form of a formaldehyde source;

$NC^P_{ES}$ = number of carbon atoms present in product stream S6 in the form of acetic acid;

[3]The yield (Y) of acrylic acid is calculated by the following formula:

$Y = 100 * (NC^P_{AS}/(NC^E_{FA} + NC^E_{ES}))$ $NC^P_{AS}$ = number of carbon atoms present in product stream S6 in the form of acrylic acid.

[4]The acrylic acid selectivity (S) is calculated by the following formula:

$S = 100 * (NC^P_{AS}/NC^P_{sum})$.

[5]The STY (space-time yield) represents the ratio of the mass flow rate of acrylic acid in stream S6 in [mass/time] to the mass of the aldol condensation catalyst in (ii) in [mass]; unit: [kg acrylic acid/kg aldol condensation catalyst/h]

TABLE 3

Catalytic results of the inventive examples at a temperature of 260° C.

| Zeolitic material according to ex. | Carbon conversion/% | AA yield/ % | AA selectivity/ % | STY/ kg/kg(cat)/h |
|---|---|---|---|---|
| 1 | 7.16 | 5.89 | 82.53 | 0.080 |
| 2 | 9.08 | 7.88 | 86.93 | 0.082 |
| 3 | 9.97 | 9.44 | 94.76 | 0.093 |

TABLE 4

Catalytic results of the comparative examples at a temperature of 290° C.

| Zeolitic material according to ex. | Carbon conversion/% | AA yield/ % | AA selectivity/ % | STY/ kg/kg(cat)/h |
|---|---|---|---|---|
| C1 | 5.01 | 3.22 | 64.24 | 0.0347 |
| C2 | 5.10 | 4.65 | 91.10 | 0.0407 |
| C3 | 3.20 | 0.77 | 24.10 | 0.0063 |
| C4 | 7.18 | 5.26 | 77.39 | 0.0583 |

TABLE 5

Catalytic results of the comparative examples at a temperature of 260° C.

| Zeolitic material according to ex. | Carbon conversion/% | AA yield/ % | AA selectivity/ % | STY/ kg/kg(cat)/h |
|---|---|---|---|---|
| C1 | 5.74 | 5.29 | 92.26 | 0.057 |
| C2 | 1.51 | 1.19 | 79.28 | 0.010 |
| C3 | 6.20 | 0.45 | 7.84 | 0.004 |
| C4 | 10.28 | 8.74 | 86.60 | 0.072 |

TABLE 6

Analysis of examples 1 to 3 with regard to NH$_3$-TPD, IR spectroscopy and water absorption

| Zeolitic material according to ex. | NH$_3$-TPD/ mmol NH$_3$/g cat. | | | FTIR | | | Water absorption/ % |
|---|---|---|---|---|---|---|---|
| | 0 to 250° C. | >250 to 500° C. | >500 to 700° C. | 3790 to 3691 cm$^{-1}$ | 3690 to 3591 cm$^{-1}$ | 3590 to 3490 cm$^{-1}$ | |
| 1 | 0.9440 | 0.3420 | 0.0180 | X | X | | |
| 2 | 0.415 | 0.331 | 0.05 | | | | 13.20 |
| 3 | 0.488 | 0.2 | 0.026 | X | X | | 19.40 |

As can be inferred from the results, inventive examples 1 to 3 show, at a higher carbon conversion, a higher yield of acrylic acid and a higher space-time yield compared to all the comparative examples C1 to C4 at a temperature of 290° C. In addition, inventive examples 1 to 3 exhibit a higher acrylic acid selectivity at a temperature of 290° C. compared to comparative examples C1, C3 and C4.

At a temperature of 260° C., inventive examples 1 to 3 show a higher carbon conversion than comparative examples C1 to C3. In addition, inventive example 3 shows a higher yield of acrylic acid than comparative examples C1 to C4, and inventive examples 1 and 2 show a higher yield of acrylic acid than comparative examples C1 to C3. In addition, inventive example 3 has a higher acrylic acid selectivity than comparative examples C1 to C4, while the value for inventive example 2 is above that for comparative examples C2 to C4 and that of inventive example 1 is above that of comparative examples C2 and C3. Finally, all the inventive examples 1 to 3 show a higher space-time yield at a temperature of 260° C. than the comparative examples C1 to C4.

Therefore, the invention provides a process for preparing acrylic acid using a formaldehyde source and acetic acid as reactants, which, through the use of a zeolitic material which does not comprise any alkali metals and alkaline earth metals, gives better catalytic results, particularly with regard to carbon conversion, yield of acrylic acid and acrylic acid selectivity, and especially with regard to space-time yield.

U.S. Provisional Patent Application No. 62/005,011, filed 30 May 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

LITERATURE CITED

Vitcha and Sims, I & EC Product Research and Development, Vol. 5, No. 1, March 1966, pages 50 to 53
Wierzchowsky and Zatorski, Catalysis Letters 9 (1991), pages 411 to 414
DE 2010 040 921 A1
DE 2010 040 923 A1
US 2013/0085294 A1

The invention claimed is:

1. A process for preparing acrylic acid, the process comprising
contacting a stream comprising a formaldehyde source and acetic acid with an aldol condensation catalyst comprising a zeolitic material having a framework structure comprising aluminum to obtain a stream comprising acrylic acid,
wherein
the framework structure of the zeolitic material comprises YO$_2$, X$_2$O$_3$ and Al$_2$O$_3$,
wherein Y is a tetravalent element; and
X is a trivalent element other than aluminum,
a total content of alkali metal and alkaline earth metal in the zeolitic material calculated as alkali metal oxide (M$_2$O) and alkaline earth metal oxide (MO), is from 0% to 0.1% by weight, based on a total weight of the zeolitic material, and
the aldol condensation catalyst further comprises from 0% to 1% by weight of vanadium, calculated as vanadium (V) oxide and based on a total weight of the aldol condensation catalyst.

2. The process according to claim 1, wherein the zeolitic material is a silicoaluminophosphate (SAPO) material or an aluminophosphate (APO) material.

3. The process according to claim 1, wherein Y is at least one tetravalent element selected from the group consisting of Si, Sn, Ti, Zr, Ge, and V.

4. The process according to claim 1, wherein X is at least one trivalent element selected from the group consisting of B, In, Ga, a transition metal of groups 3 to 12.

5. The process according to claim 1, wherein the zeolitic material is at least partly in an H form.

6. The process according to claim 5, wherein
a molar NH$_4^+$:(Al+X) ratio of the zeolitic material, when the zeolitic material is saturated with NH$_3$, is from 0.01:1 to 1:1.

7. The process according to claim 1, wherein the zeolitic material comprises at least one non-framework element Z selected from the group consisting of Ti, Zr, Nb, Ta, Cr, Mo, W, Mn, Fe, Co, Ni, Zn, Ga, Ge, In, Sn, Pb, P, N, and S and any combination thereof.

8. The process according to claim 7, wherein the at least one non-framework element Z is selected from the group consisting of N, P and S, wherein the at least one non-framework element is present at least partly in an oxidic form.

9. The process according to claim 1, wherein the zeolitic material has a structure selected from the group consisting of BEA, MFI, MWW, FAU, MEL, MTN, RRO, CDO LTL, MOR, AFI, FER, LEV and any combination thereof.

10. The process according to claim 1, wherein the aldol condensation catalyst further comprises a binder material.

11. The process according to claim 1, wherein the aldol condensation catalyst is in a form of shaped bodies, is in a star shape, is in a tablet form, is in a form of spheres, or is in a form of hollow cylinders.

12. The process according to claim 1, wherein the contacting is effected at a temperature of from 200 to 400° C.

13. The process according to claim 1, wherein
a space-time yield in the contacting is from 0.01 to 2.5 kg/kg/h, and
the space-time yield is defined as kg(acrylic acid)/kg (aldol condensation catalyst)/h.

14. The process according to claim 1, wherein the formaldehyde source is an anhydrous formaldehyde source.

15. The process according to claim 1, wherein
a temperature-programmed desorption with $NH_3$ ($NH_3$-TPD) of the zeolitic material has a desorption spectrum with a desorption maximum within at least one of temperature ranges of from 0 to 250° C., from 251 to 500° C., or from 501 to 700° C., and
following deconvolution of the desorption spectrum, the desorption maximum in the temperature range of 0 to 250° C. has a concentration of desorbed $NH_3$ in a range of from 0.05 to 2.0 mmol/g, the desorption maximum in the temperature range of 251 to 500° C. has a concentration of desorbed $NH_3$ in a range of from 0.05 to 1.5 mmol/g, and the desorption maximum in the temperature range of 501 to 700° C. has a concentration of desorbed $NH_3$ in a range of from 0.001 to 0.5 mmol/g, wherein the concentration of desorbed $NH_3$ is defined as mmol(desorbed $NH_3$)/g(zeolitic material).

* * * * *